(12) United States Patent
Koo

(10) Patent No.: US 10,099,102 B1
(45) Date of Patent: Oct. 16, 2018

(54) ATHLETIC SENSOR SYSTEM

(71) Applicant: Jason Koo, Manhattan Beach, CA (US)

(72) Inventor: Jason Koo, Manhattan Beach, CA (US)

(*) Notice: Subject to any disclaimer, the term of this patent is extended or adjusted under 35 U.S.C. 154(b) by 192 days.

(21) Appl. No.: 15/017,563

(22) Filed: Feb. 5, 2016

Related U.S. Application Data

(60) Provisional application No. 62/112,599, filed on Feb. 5, 2015.

(51) Int. Cl.
| | |
|---|---|
| *A63B 60/46* | (2015.01) |
| *A63B 69/36* | (2006.01) |
| *A63B 71/06* | (2006.01) |
| *A63B 69/00* | (2006.01) |

(52) U.S. Cl.
CPC .......... *A63B 60/46* (2015.10); *A63B 69/0002* (2013.01); *A63B 69/36* (2013.01); *A63B 71/0619* (2013.01); *A63B 2069/0008* (2013.01); *A63B 2220/12* (2013.01); *A63B 2220/16* (2013.01); *A63B 2220/40* (2013.01); *A63B 2220/44* (2013.01); *A63B 2220/833* (2013.01); *A63B 2220/836* (2013.01); *A63B 2225/50* (2013.01)

(58) Field of Classification Search
CPC ...... A63B 60/46; A63B 69/0002; A63B 69/36
See application file for complete search history.

(56) References Cited

U.S. PATENT DOCUMENTS

| | | | | |
|---|---|---|---|---|
| 6,224,493 | B1* | 5/2001 | Lee | A63B 69/3614 473/221 |
| 6,739,981 | B1* | 5/2004 | Lin | A63B 69/3632 473/219 |
| 7,602,301 | B1 | 10/2009 | Stirling | |
| 7,736,242 | B2 | 6/2010 | Stites | |
| 7,821,407 | B2 | 10/2010 | Shears | |
| 8,409,025 | B2 | 4/2013 | Stites | |
| 8,465,376 | B2 | 6/2013 | Bentley | |
| 2006/0166737 | A1* | 7/2006 | Bentley | A61B 5/1122 463/30 |
| 2010/0216563 | A1* | 8/2010 | Stites | A63B 69/3614 473/223 |
| 2011/0230273 | A1 | 9/2011 | Niegowski | |
| 2012/0139731 | A1 | 6/2012 | Razoumov | |
| 2013/0324274 | A1 | 12/2013 | Stites | |

(Continued)

*Primary Examiner* — Dmitry Suhol
*Assistant Examiner* — Brandon Gray
(74) *Attorney, Agent, or Firm* — Quickpatents, LLC; Kevin Prince

(57) ABSTRACT

A sensor system for detecting aspects of a person's swing of a sporting implement having proximal and distal ends displays the aspects of the person's swing on a portable electronic device. The system includes a distal enclosure, a proximal enclosure, and a software application resident on the portable electronic device. The proximal and distal enclosures are fixable with the proximal and distal ends, respectively, of the sporting implement, and two additional hip enclosures may be include for fixing with the person's hips. Each enclosure includes a power source that powers a sensing circuit having at least one sensor and a transmitter. The software application is adapted to receive the sensor data from the sensing circuits and display aspects of the person's swing on a display thereof as derived from the sensor data. Embodiments adapted for use with golf clubs, sporting racquets, and baseball bats are disclosed.

20 Claims, 8 Drawing Sheets

(56) References Cited

U.S. PATENT DOCUMENTS

| | | | |
|---|---|---|---|
| 2014/0073446 A1* | 3/2014 | Davenport | A63B 24/0006 473/223 |
| 2014/0357391 A1 | 12/2014 | Parke | |
| 2014/0357392 A1* | 12/2014 | Goel | G06K 9/00342 473/223 |

* cited by examiner

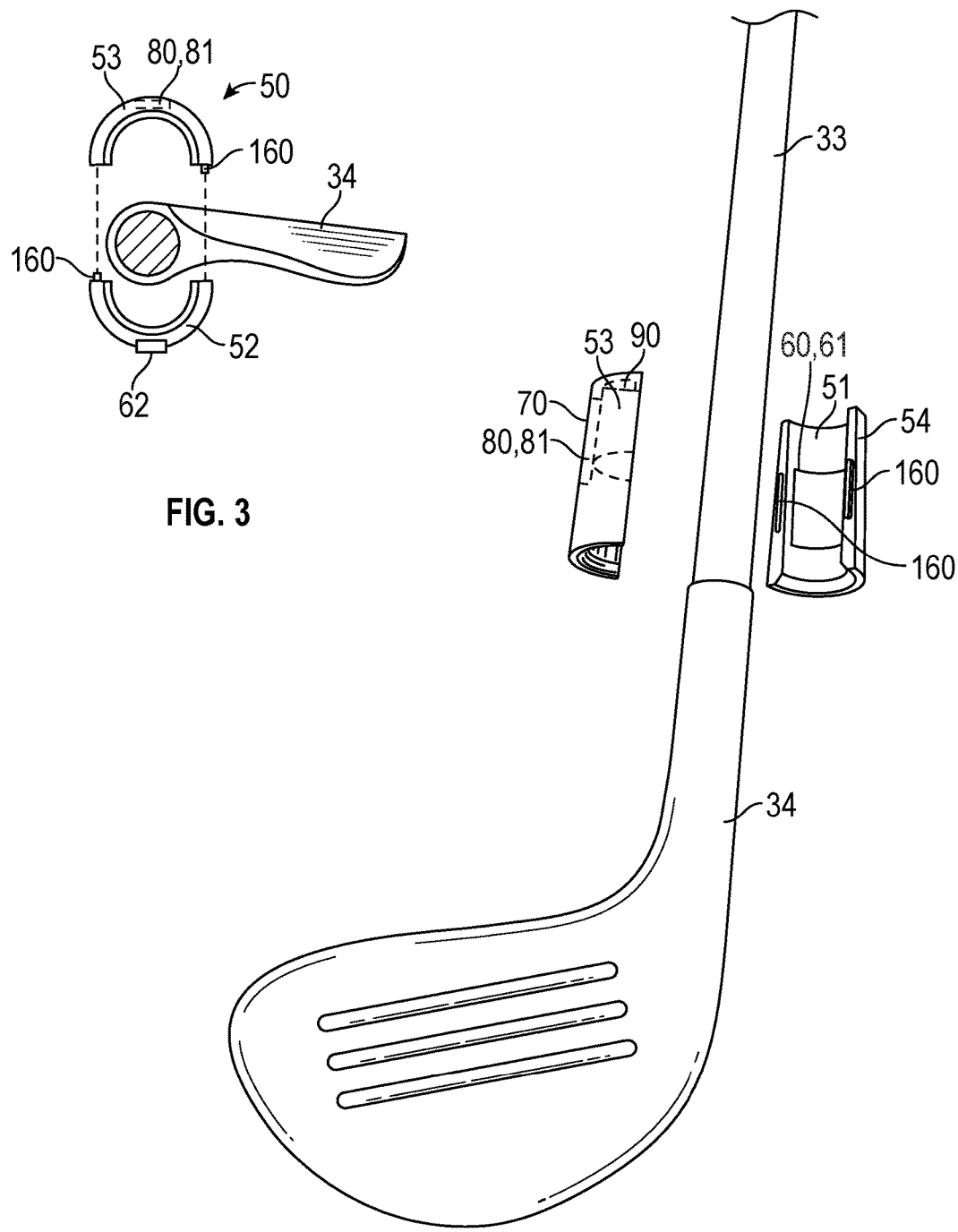

ATHLETIC SENSOR SYSTEM

CROSS-REFERENCE TO RELATED APPLICATIONS

This application claims the benefit of U.S. Provisional Patent Application 62/112,599, filed on Feb. 5, 2015, and incorporated herein by reference.

STATEMENT REGARDING FEDERALLY SPONSORED RESEARCH AND DEVELOPMENT

Not Applicable.

FIELD OF THE INVENTION

This invention relates to sports training, and more particularly to a sensor system for improving a user's swing of sporting implements.

DISCUSSION OF RELATED ART

With the advent of inexpensive accelerometers that are now included in a variety of electronic devices, the ability to detect acceleration, orientation and speed of a sporting implement such as a golf club has become more practical. Indeed several products that measure such parameters are available from Zepp US Inc. of Los Gatos, Calif.; Mobitee.com; and Swingbyte of Chicago, Ill.

None of the prior art devices, however, teaches a system having sensors at both ends of the sporting implement, and none teaches locating a sensor close to the distal end of the sporting implement. As a result, the speed of a golf club head, for example, is derived from assumptions made about the length of the golf club shaft. Aspects of the swing such as flex of the club are impossible to measure with a single sensor located at the handle.

Further, none of the prior art devices teaches sensors attached to the person for determining attributes of the swing such as weight shift, hip rotation, and the like.

Therefore, there is a need for a system that can measure aspects of a sporting implement swing at both ends of the sporting implement and on at least two areas of the person. Such a needed invention would be relatively inexpensive and easy to install on the sporting implement, preferably in a permanent or semi-permanent manner. Such a needed system would be relatively easy to use with a wide variety of currently available portable electronic devices. The present invention accomplishes these objectives.

SUMMARY OF THE INVENTION

The present device is a sensor system for detecting aspects of a person's swing of a sporting implement that has a proximal end and a distal end. The system displays the aspects of the person's swing on a portable electronic device, such as a so-called "smart phone," tablet or laptop computer, or the like.

The system includes a distal enclosure, a proximal enclosure, and a software application resident on the portable electronic device. The distal enclosure is fixable proximate the distal end of the sporting implement and houses a first power source that powers a first sensing circuit, which includes at least one sensor and a transmitter that is adapted to transmit data from the at least one sensor of the first sensing circuit to the portable electronic device.

Similarly, the proximal enclosure is fixable proximate the proximal end of the sporting implement and houses a second power source that powers a second sensing circuit. The second sensing circuit includes at least one sensor and a transmitter that is adapted to transmit data from the at least one sensor of the second sensing circuit to the portable electronic device.

Each sensing circuit includes a non-transient memory that retains a unique sensor identifier that is transmitted along with the data from each of the at least one sensor to the portable electronic device. The software application is adapted to receive the sensor data from the first and second sensing circuits and to display aspects of the person's swing on a display thereof as derived from the sensor data.

In a first embodiment, the sporting implement is a golf club that has a shaft and a club head at the distal end thereof. In such an embodiment the distal enclosure may take the form of a two-part ferrule that is fixable about the golf club shaft at the club head. The power source in such an embodiment is preferably a rechargeable battery fixed with a first part of the two-part ferrule. Similarly, the first sensing circuit is fixed with or contained within a second part of the two-part ferrule. The first and second parts, of the ferrule are mutually connectable at a pair of electric contacts that conduct power from the power source to the first sensing circuit. The proximal enclosure in such an embodiment preferably includes a golf club grip that is fixable about the proximal end of the golf club shaft.

In such an embodiment, the at least one sensor of both the distal enclosure and proximal enclosure preferably includes a three-axis accelerometer, suitable for detecting acceleration of the golf club head in all three-axes. One of the at least one sensors of the distal enclosure, in one embodiment, is a microphone and/or a shock or vibration sensor that detects the impact sound of the golf club head with the golf ball. In another embodiment, at least one of the sensors is a 3-axis gyroscope.

Two hip enclosures may be included for fixing proximate the hips of the person. Such hip enclosures further include a third power source powering a third sensing circuit that includes at least one sensor and transmitter. As such, aspects of a person's swing are displayable on the portable electronic device such as the shift of the person's weight from side to side and rotation of the person's hips during the swing.

In one embodiment the sporting implement is a sports racquet that includes a racquet head at the distal end thereof and a racquet handle at the proximal end thereof. In such an embodiment, the distal enclosure may be adapted to cover and protect at least a portion of racquet strings that are exposed at the distal end of the racquet head. The proximal enclosure includes a sports racquet grip fixable about the proximal end of the racquet handle of the sports racquet.

In one embodiment the sporting implement is a baseball bat, preferably of the type having a concave distal end. In such an embodiment, the distal enclosure may be fixable to the concave distal end of the baseball bat such that the distal enclosure does not protrude outwardly from the distal end. In such an embodiment, the distal enclosure and the proximal enclosure may each include a central screw aperture through which a mechanical fastener, such as a screw, may be inserted to fix the enclosure, to the baseball bat. In the case of aluminum baseball bats, the enclosure may be affixed to the proximal and distal ends of the baseball bat with a strong adhesive, metal screw, or other suitable mechanical fastener.

The present invention is a system that can measure aspects of a sporting implement swing at both ends of the sporting implement and on at least two areas of the person. The present system is relatively inexpensive and easy to install on the sporting implement in a subtle and permanent or semi-permanent manner. The present invention is relatively easy to use with a wide variety of currently available portable electronic devices. Other features and advantages of the present invention will become apparent from the following more detailed description, taken in conjunction with the accompanying drawings, which illustrate, by way of example, the principles of the invention.

DESCRIPTION OF THE DRAWINGS

FIG. 2 is an exploded side perspective view of the embodiment of FIG. 1;

FIG. 3 is an exploded top view of the embodiment of FIG. 1;

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 9:
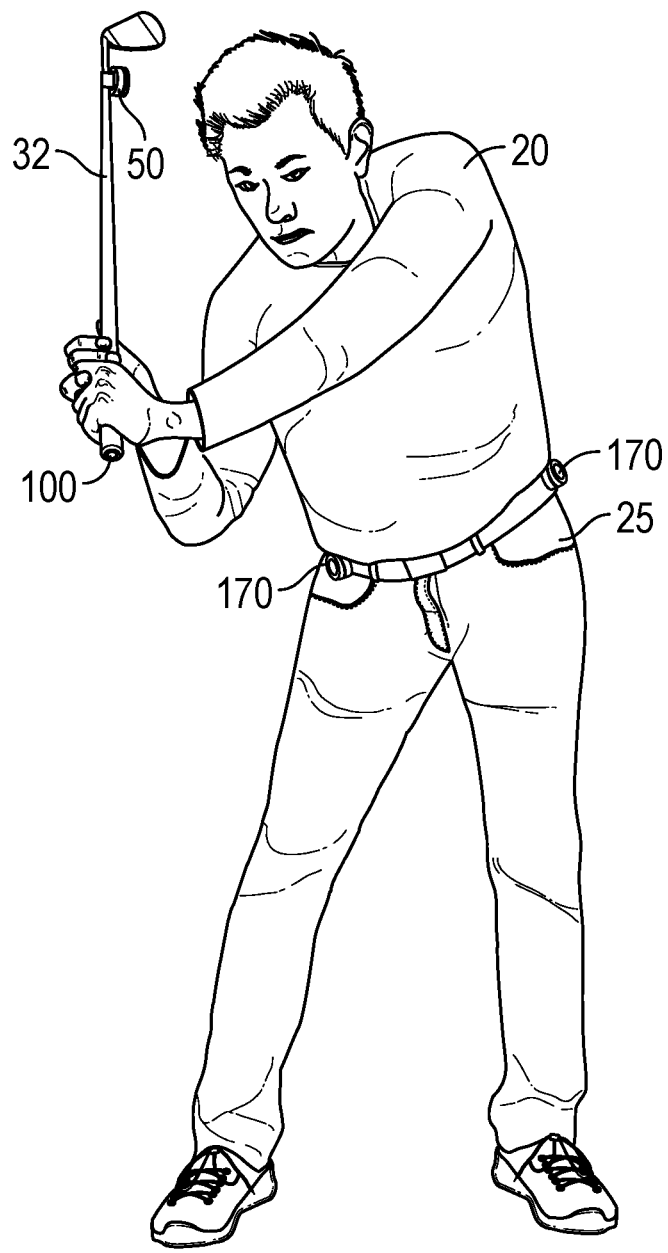
FIG. 9 is a front elevational view of a person with proper weight balance, detectable by the embodiment of FIG. 7.
Figure 10:
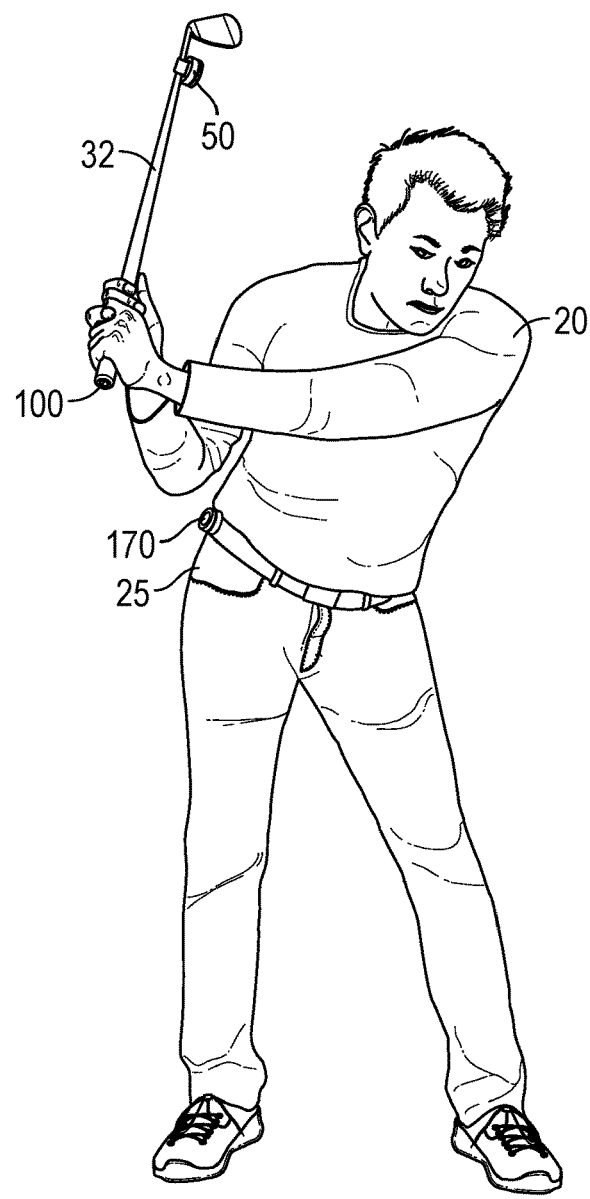
FIG. 10 is a front elevational view of a person with improper weight balance, detectable by the embodiment of FIG. 7.

FIGS. 1A-4 illustrate a sensor system 10 for detecting aspects of a swing made by a person 20 (FIGS. 9 and 10) of a sporting implement 30 that has a proximal end 31 and a distal end 39. The system 10 displays the aspects of the person's swing on a portable electronic device 40 that has at least a transceiver 44, a computer circuit 45 that includes a non-volatile memory 46, and a display 47. Such a portable electronic device may be, for example, a so-called "smart phone" such as an Apple® brand iPhone® or an Android® type of portable electronic device, a tablet computer, a laptop computer, or the like.

The system 10 includes a distal enclosure 50, a proximal enclosure 100, and a software application 150 resident on the portable electronic device 40. The software application 150 may be adapted to show data in the form of numbers, as well as to graphically model parameters such as by showing a simulated slow-motion swing plane or implement rotation throughout the swing. As such, the person's swing of the sports implement may be modeled and replayed for the person so as to show the person possible aspects of the swing that need improvement, or aspects of the swing that are being performed properly and optimally.

The distal enclosure 50 is fixable proximate the distal end 39 of the sporting implement 30 and houses a first power source 60, such as a battery 61, that powers a first sensing circuit 70. The first sensing circuit 70 includes at least one sensor 80 and a transmitter 90 that is adapted to transmit data from the at least one sensor 80 of the first sensing circuit 70 to the portable electronic device 40.

Similarly, the proximal enclosure 100 is fixable proximate the proximal end 31 of the sporting implement 30 and houses a second power source 110, such as the battery 61, that powers a second sensing circuit 71. The second sensing circuit 71 includes at least one sensor 80 and a transmitter 90 that is adapted to transmit data from the at least one sensor 80 of the second sensing circuit 71 to the portable electronic device 40.

Each sensing circuit 70, 71 includes a central processing unit (CPU) 120 and a non-transient memory 130 that retains a unique sensor identifier that is transmitted along with the data from each of the at least one sensor 80 to the portable electronic device 40. As such, each golf club 32 in a set of golf clubs 32 may be outfitted with the system 10, the software application 150 previously set to know which two unique identifiers belong to the enclosure on each end 31,39 of each club 32. The transmitter 90 of each enclosure 50,100 preferably utilizes a Bluetooth-type wireless protocol to transmit the sensor data to the portable electronic device 40, but other suitable wireless protocols may be used such as WiFi, for example.

The software application 150 is adapted to receive the sensor data from the first and second sensing circuits 70, 71 through the transceiver 44 and computer circuit 45 of the portable electronic device 40, and to display aspects of the person's swing on the display 47 thereof as derived from the sensor data. In an embodiment wherein each golf club 32 in a set of clubs 32 includes the distal and proximal enclosures 50,100, the software application 150 is further able to keep score in a game of golf (excluding penalty strokes), particularly when coupled with a GPS function of the portable electronic device 40. Only swings of the golf club 32 that actually strike a golf ball are counted, based on accelerometer 81 data or other sensor data. In one embodiment, a microphone (not shown) of the portable electronic device 40 listens for the strike of the club head 34 with the golf ball and compares that information with the sensor data coming from the enclosures 50,100. From such data it is clear which club 32 of the set is being used to strike the ball, and based on GPS data from shot to shot the average range of each club 32 may be, over time, ascertained by the software application 150. Additionally, one of the sensors 80 may be a Micro-GPS 84 sensor for determining minute movements of any of the enclosures 50, 100.

Figures 1A, 1B:
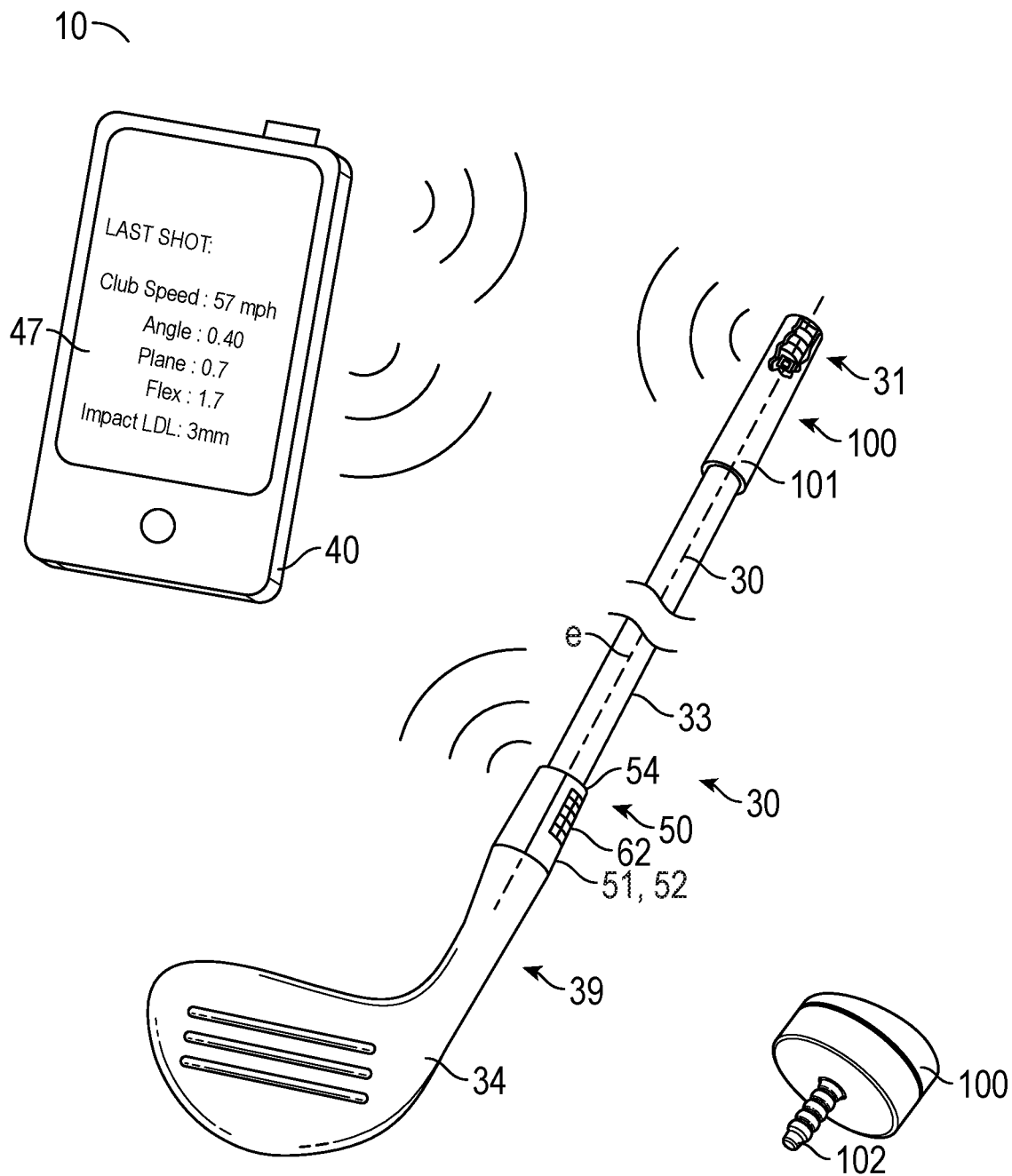
FIG. 1A is a perspective view of one embodiment of the invention, wherein a sporting implement is a golf club.
FIG. 1B is an enlarged, alternate embodiment of a distal enclosure of the invention.
Figure 4:
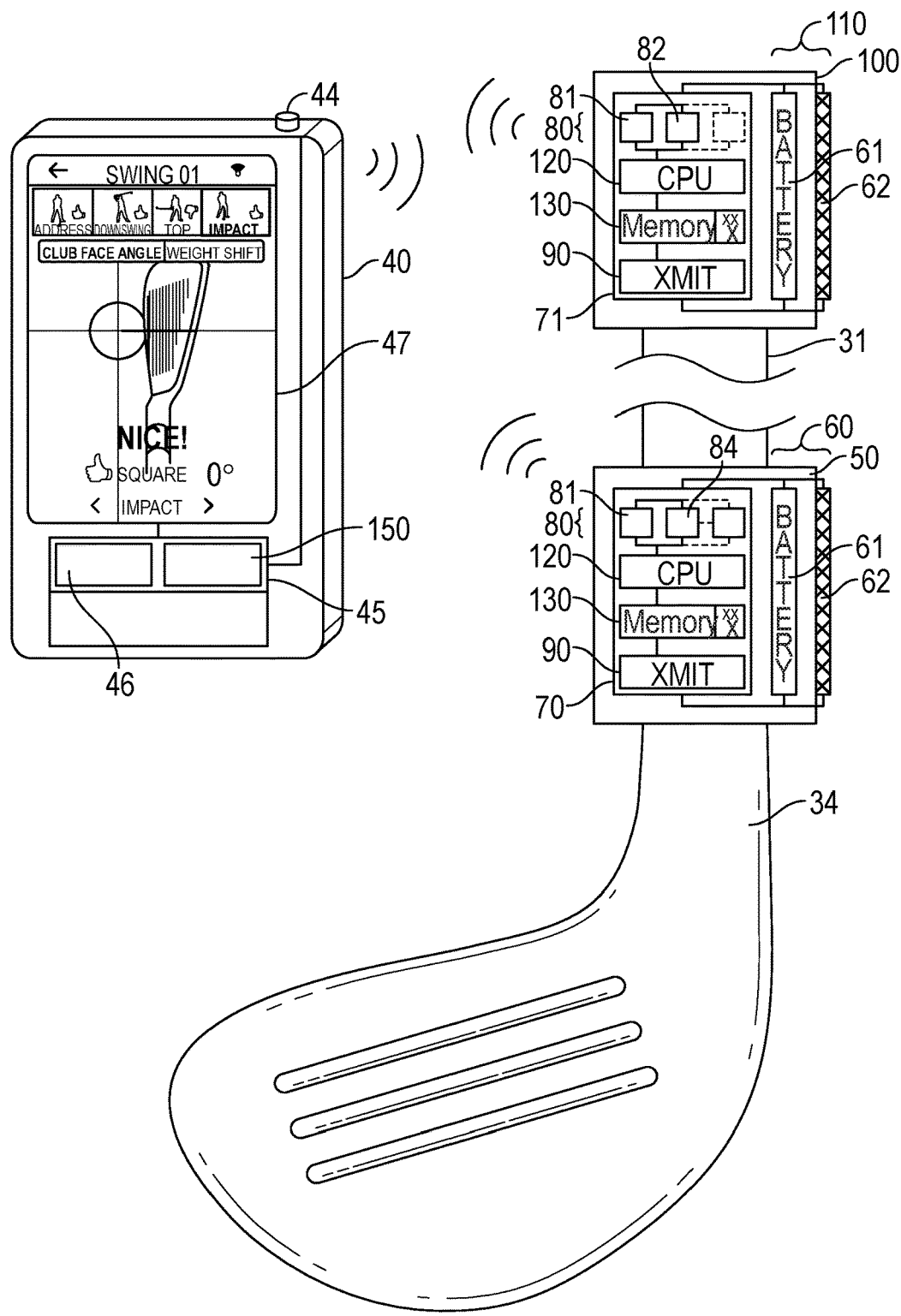
FIG. 4 is a diagram of the components of the embodiment of FIG. 1.
Figure 11:
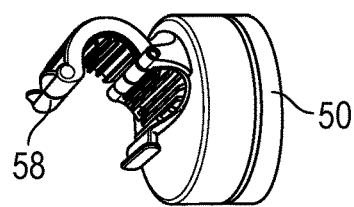
FIG. 11 is an alternate embodiment of the proximal enclosure of the invention that snaps onto the shaft of a golf club.

In a first embodiment, the sporting implement 30 is a golf club 32 that has a shaft 33 and a club head 34 at the distal end 39 thereof. In such an embodiment the distal enclosure 50 may take the form of a two-part ferrule 51 that is fixable about the golf club shaft 33 at the club head 34 (FIGS. 1A, 2 and 3). The power source 60 in such an embodiment is preferably a rechargeable battery 61 fixed with a first part 52 of the two-part ferrule 51. Similarly, the first sensing circuit 70 is fixed with or contained within a second part 53 of the two-part ferrule 51. The first and second parts 52,53 of the ferrule 51 are mutually connectable at a pair of electric contacts 160 that conduct power from the power source 61 to the first sensing circuit 70. At least one solar cell 62 (FIGS. 1A and 4) may be fixed with an outer surface 54 of the first part 52 of the ferrule 51 to recharge the battery 61 when exposed to light. In such an embodiment, the battery 61, solar cell 62, and first sensing circuit 70 are all preferably weight-balanced about the ferrule 51 so that the center of gravity of the ferrule 51 lies substantially along the longitudinal axis of the club shaft 33 when the ferrule 51 is mounted to the shaft 33, so that the balance of the golf club 32 is not adversely affected and the impact to the person's golf club swing is minimized. Alternately the distal enclosure 50 may include a mechanical clamp arrangement 58 (FIG. 11) for selectively and temporarily affixing with the shaft 33 of the golf club 32. As such, the distal enclosure 50 may be moved to different clubs 32.

The proximal enclosure 100 can include a golf club grip 101 that is fixable about the proximal end 31 of the golf club shaft 33. Such a grip 101 may include one or more of the solar cells 62 for powering the second sensing circuit 71 and recharging the second power source 110, preferably also one of the rechargeable batteries 61. Alternately the proximal enclosure 100 includes an insert plug 102 (FIG. 1B) for inserting into the existing grip 101 of the golf club 32.

In such an embodiment, the at least one sensor 80 of both the distal enclosure 50 and proximal enclosure 100 preferably includes a three-axis accelerometer 81, suitable for detecting acceleration of the golf club head 34 and proximal end 31 in all three axes. Alternately, three accelerometers 81 maybe included and all aligned at least partially along three orthogonal axes. As such, aspects of the person's swing that may be analyzed based on the data from the accelerometer 81 include at least the acceleration of the club head 34 on both the backswing and swing of the golf club 32, the orientation of the golf club 32 throughout the swing, the flatness of the plane of the golf club 32 throughout the swing, the angle of the club head 34 at the point of impact, the centeredness of the ball when impacting the club head 34 as measured by the resultant vibration of the club head 34 after ball impact, the force of impact of the ball with the club head 34, the extent of the backswing and follow through, the person's wrist orientation throughout the swing, and the flex and torsion of the club shaft 33 throughout the swing.

One of the at least one sensors 80 of the distal enclosure 50, in one embodiment, is a microphone that detects the impact sound of the golf club head 34 with the golf ball (not shown). Alternately, a shock or vibration sensor (not shown) may be used. As such the position of the club head 34 at impact can be derived, in addition to deceleration of the club head 34 at impact. In another embodiment, at least one of the sensors 80 is a 3-axis gyroscope 82, such as a MEMS motion sensor or the like.

Figure 5:
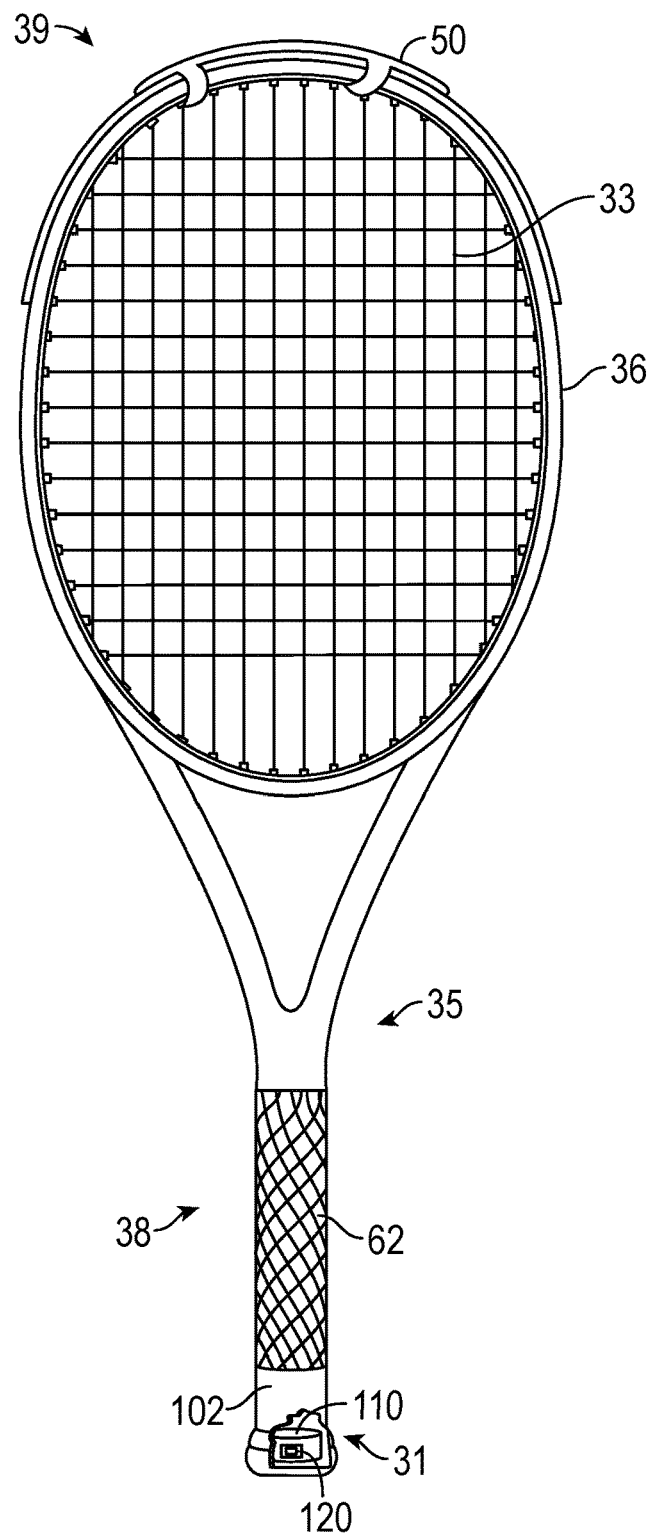
FIG. 5 is a front elevational view of an alternate embodiment of the invention, wherein the sporting implement is a tennis racquet.

In one embodiment the sporting implement is a sports racquet 35, such as a tennis racquet 35 (FIG. 5), that includes a racquet head 36 at the distal end 39 thereof and a racquet handle 38 at the proximal end 31 thereof. In such an embodiment, the distal enclosure 50 may be adapted to cover and protect at least a portion of racquet strings 37 that are exposed at the distal end 39 of the racquet head 36. The proximal enclosure 100 includes a sports racquet grip 102 fixable about the proximal end 31 of the racquet handle 38 of the sports racquet 35.

Figure 6:
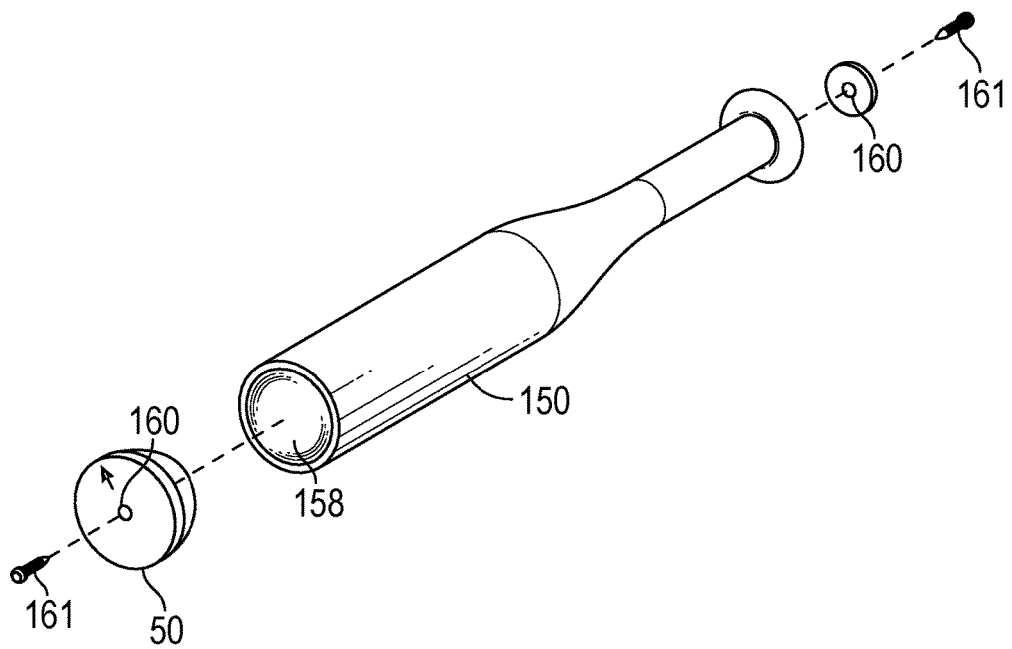
FIG. 6 is an exploded perspective view of another alternate embodiment of the invention, wherein the sporting implement is a baseball bat.

The sensors 80 in the distal enclosure 50 of such an embodiment may include an accelerometer 81 aligned to detect changes in rotation of the racquet 35, among additional parameters of a person's racquet stroke, such as acceleration of the racquet head 36 on both the backswing and swing of the racquet 35, the orientation of the racquet 35 throughout the swing, the flatness of the plane of the racquet 35 throughout the swing, the angle of the racquet head 36 at the point of impact, the centeredness of the ball when impacting the racquet head 36 as measured by the resultant vibration of the racquet head 36 after ball impact, the force of impact of the ball with the racquet head 36, the extent of the backswing and follow through, and the person's wrist orientation throughout the swing In one embodiment the sporting implement is a baseball bat 150 (FIG. 6), preferably of the typing having a concave distal end 158. In such an embodiment, the distal enclosure 50 may be fixable to the concave distal end 158 of the baseball bat 150 such that the distal enclosure does not protrude outwardly from the distal end 158. As such, the chance of a baseball (not shown) impacting the distal enclosure 50 during a swing of the bat 150 is reduced. In such an embodiment, the distal enclosure 50 and the proximal enclosure 100 may each include a central screw aperture 160 through which a mechanical fastener 161, such as a screw, may be inserted to fix the enclosure 50,100 to the baseball bat 150. In the case of aluminum baseball bats 150, the enclosure 50,100 may be affixed to the proximal and distal ends 31,39 of the baseball bat 150 with a strong adhesive, metal screw, or other suitable mechanical fastener.

The sensors 80 in the distal enclosure 50 of such an embodiment may include an accelerometer 81 aligned to detect changes speed of the swing of the baseball bat 150, as well as other parameters such as acceleration of the baseball bat 150 on both the backswing and swing of the baseball bat 150, the orientation of the baseball bat 150 throughout the swing, the flatness of the plane of the baseball bat 150 throughout the swing, the centeredness of the ball when impacting the baseball bat 150 as measured by the resultant vibration of the baseball bat 150 after ball impact, the force of impact of the ball with the baseball bat 150, the extent of the backswing and follow through, and the person's wrist orientation throughout the swing.

Figure 7:
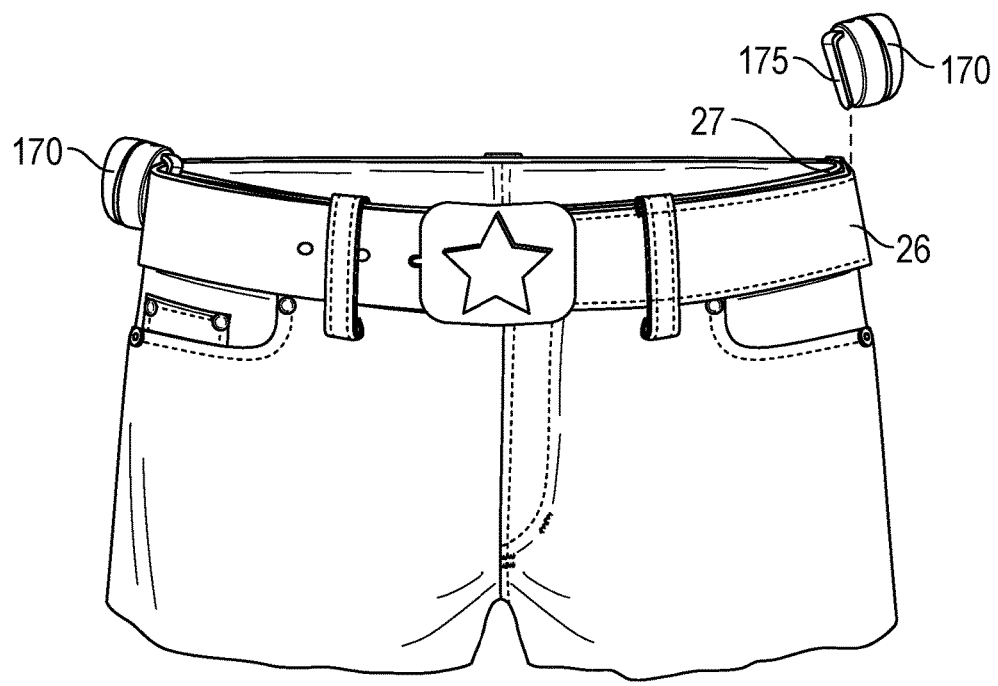
FIG. 7 is an exploded front elevational view of another alternate embodiment of the invention, further including two hip enclosures attached to a person's belt or garment.
Figure 8:
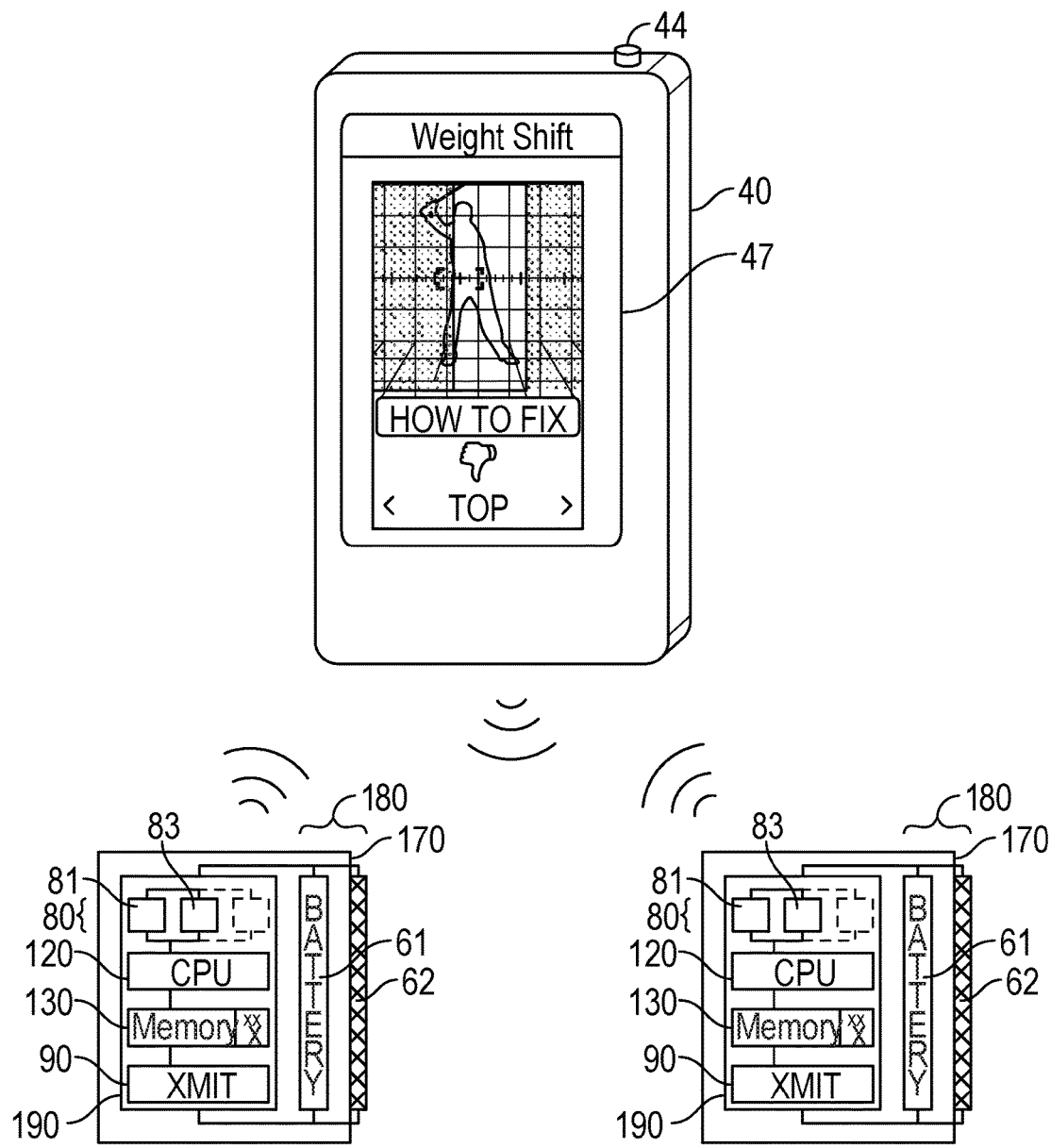
FIG. 8 is a diagram of the additional components of the embodiment of FIG. 7.

In one preferred embodiment, the sensor system 10 includes first and second hip enclosures 170 (FIG. 7), each fixable proximate opposing hips 25 of the person 20 (FIS. 9 and 10), such as with a belt clip 175 for attachment to a person's belt 26 or the waistline of his pants 27, for example. Each hip enclosure 170 includes a third power source 180 powering a third sensing circuit 190 (FIG. 8). The third sensing circuit 190 includes at least one of the sensors 80 and transmitters 90, the transmitter 90 adapted to transmit data from the at least one sensor 80 to the portable electronic device 40. Preferably the sensors 80 included with the hip enclosures 170 are the 3-axis accelerometer 81 and a 3-axis magnetometer 83 for sensing orientation of the enclosure 170. The hip enclosures 170 are preferably fixed proximate the person's hips 25 as opposed to at his front or rear sides to reduce the chance that metallic belt buckles or the like might interfere with such a magnetometer 83.

As such, one of the aspects of the person's swing displayable on the portable electronic device 40 is the shift of the person's body weight from side to side and rotation of the person's hips 25 during the swing. If the hip enclosures 170 shift laterally during the swing, which is evidence that an improper weight shift occurred to the person's trailing foot (FIG. 10), then the person 20 may be alerted to the improper weight shift on the portable electronic device 40. Alternately, if the weight of the person 20 is maintained on his leading foot (FIG. 9), then the person 20 may be notified that his weight balance during the swing was proper.

While a particular form of the invention has been illustrated and described, it will be apparent that various modifications can be made without departing from the spirit and scope of the invention. For example, additional embodiments for other sporting implements 30 may be devised, such as for hockey sticks, cricket bats, lacrosse sticks, javelins, pool cues, ski poles, ping pong paddles, fencing foils, sabers and epees, throwing batons, archery arrows, boat oars, and even participant appendages such as arms and legs so that arm and leg positions and movements during sporting endeavors such as soccer, football, boxing, gymnastics, handball, martial arts, swimming, diving, skating, volleyball, and water polo may be ascertained. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference.

Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A sensor system for detecting aspects of a person's swing of a sporting implement having a proximal end and a distal end, and displaying aspects of the person's swing on a portable electronic device having at least a transceiver, a computer circuit that includes a non-volatile memory, and a display, the sensor system comprising:

a distal enclosure fixable to a distal external surface of the sporting implement proximate the distal end of the sporting implement, the distal enclosure housing a first power source powering a first sensing circuit housed within the distal enclosure, the first sensing circuit including at least one sensor and transmitter, the transmitter of the first sensing circuit adapted to transmit data from the at least one sensor of the first sensing circuit to the portable electronic device, the first sensing circuit further including a first non-transient memory that retains a first unique sensor identifier that is transmitted, along with the data from the at least one sensor of the first sensing circuit, to the portable electronic device;

a proximal enclosure separated and spaced from the distal enclosure, the proximal enclosure fixable to a proximal external surface of the sporting implement proximate the proximal end of the sporting implement, the proximal enclosure housing a second power source powering a second sensing circuit housed within the proximal enclosure, the second sensing circuit including at least one sensor and transmitter, the transmitter of the second sensing circuit adapted to transmit data from the at least one sensor of the second sensing circuit to the portable electronic device, the second sensing circuit further including a second non-transient memory that retains a second unique sensor identifier that is transmitted, along with the data from the at least one sensor of the second sensing circuit, to the portable electronic device; and a software application resident on the portable electronic device, the software application adapted to receive the sensor data from the first and second sensing circuits and adapted to display aspects of the person's swing on the display of the portable electronic device as derived from the sensor data.

2. The sensor system of claim 1 wherein the sporting implement is a golf club, a golf club shaft of the golf club including at least the distal external surface and the proximal external surface, and wherein the distal enclosure is a two-part ferrule fixable about the distal external surface of the golf club shaft at a club head disposed at the distal end of the golf club.

3. The sensor system of claim 2 wherein the first power source is a battery contained in a first part of the two-part ferrule, and wherein the first sensing circuit is contained within a second part of the two-part ferrule, the first and second parts of the two-part ferrule being mutually connectable at a pair of electric contacts that conduct power from the first power source to the first sensing circuit.

4. The sensor system of claim 3 wherein at least one solar cell is fixed with an outer surface of the first part of the two-part ferrule, the at least one solar cell adapted to recharge the battery when exposed to light.

5. The sensor system of claim 2 wherein the proximal enclosure includes a golf club grip fixable about the proximal external surface of the golf club shaft proximate the proximal end of the golf club.

6. The sensor system of claim 1 wherein one of the at least one sensors of the first and second sensing circuits is an accelerometer.

7. The sensor system of claim 6 wherein the accelerometer is a 3-axis accelerometer.

8. The sensor system of claim 1 wherein one of the at least one sensors of the first and second sensing circuits is a 3-axis gyroscope.

9. The sensor system of claim 1 wherein the transmitters of the first and second sensing circuits each utilize a Bluetooth-based protocol.

10. The sensor system of claim 2 wherein a mass of the first power source and a mass of the first sensing circuit are substantially balanced about the two-part ferrule, whereby a center of gravity of the two-part ferrule is aligned with a longitudinal axis of the golf club shaft.

11. The sensor system of claim 1 wherein the sporting implement is a sports racquet, a racquet head of the sports racquet including at least the distal external surface, and wherein the distal enclosure is fixable with the distal external surface of the racquet head proximate the distal end of the sports racquet.

12. The sensor system of claim 11 wherein the racquet head includes strings, and wherein the distal enclosure covers and protects at least a portion of the strings exposed at the distal end of the sports racquet.

13. The sensor system of claim 11 wherein a racquet handle of the sports racquet includes at least the proximal external surface, and wherein the proximal enclosure includes a sports racquet grip fixable about the proximal external surface of the racquet handle proximate the proximal end of the sports racquet.

14. The sensor system of claim 1 wherein the sporting implement is a baseball bat, a concave end portion of the baseball bat including at least the distal external surface and a proximal end portion of the baseball bat including at least the proximal external surface, wherein the distal enclosure is fixable to the distal external surface of the concave end portion at the distal end of the baseball bat, and wherein the proximal enclosure is fixable to the proximal external surface of the proximal end portion at the proximal end of the baseball bat.

15. The sensor system of claim 14 wherein the distal enclosure is fixable to the distal external surface within the concave end portion of the baseball bat and does not protrude outwardly from the concave end portion when fixed with the baseball bat.

16. The sensor system of claim 15 wherein the distal enclosure includes a central screw aperture through which a mechanical fastener traverses to hold the distal enclosure within the concave end portion at the distal end of the baseball bat.

17. The sensor system of claim 1 further including first and second hip enclosures each configured to be fixable proximate opposing hips of the person, each of the first and second hip enclosures housing a third power source powering a third sensing circuit, the third sensing circuit including at least one sensor and transmitter, the transmitter of the third sensing circuit adapted to transmit data from the at least one sensor of the third sensing circuit to the portable electronic device, whereby one of the aspects of the person's swing displayable on the portable electronic device is a shift of the person's weight from side to side and rotation of the person's hips during the swing of the sporting implement.

18. The sensor system of claim 17 wherein each of the first and second hip enclosures include a belt clip for attachment to a person's belt or a waistline of the person's pants.

19. The sensor system of claim 17 wherein one of the at least one sensors in each of the first and second hip enclosures is a 3-axis magnetometer adapted to detect change in orientation of the respective hip enclosure.

20. The sensor system of claim 1 wherein one of the at least one sensors of the first and second sensing circuits is a micro-GPS sensor adapted to detect movement within 0.5 to 2.0 cm.

* * * * *